US009686509B2

United States Patent
Lee et al.

(10) Patent No.: US 9,686,509 B2
(45) Date of Patent: Jun. 20, 2017

(54) SUPPORTING PATIENT-CENTEREDNESS IN TELEHEALTH COMMUNICATIONS

(71) Applicant: KONINKLIJKE PHILIPS N.V., Eindhoven (NL)

(72) Inventors: Matthew Len Lee, New York, NY (US); Berthel Floyne Tate, Brandywine, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1 day.

(21) Appl. No.: 14/706,110

(22) Filed: May 7, 2015

(65) Prior Publication Data

US 2015/0358583 A1 Dec. 10, 2015

Related U.S. Application Data (60) Provisional application No. 60/010,120, filed on Jun. 10, 2014.

(51) Int. Cl.

| | |
|---|---|
| *H04N 7/14* | (2006.01) |
| *H04N 7/15* | (2006.01) |
| *G06F 19/00* | (2011.01) |
| *H04L 12/18* | (2006.01) |
| *G10L 21/003* | (2013.01) |

(52) U.S. Cl.
CPC ........... *H04N 7/15* (2013.01); *G06F 19/3425* (2013.01); *H04L 12/1813* (2013.01); *G10L 21/003* (2013.01)

(58) Field of Classification Search
USPC ... 348/14.08, 14.09, 14.1, 211.12, 208.3, 77, 348/78, E7.08, E13.047
See application file for complete search history.

(56) References Cited

U.S. PATENT DOCUMENTS

| | | | |
|---|---|---|---|
| 8,290,776 B2 | 10/2012 | Moriwaki et al. | |
| 8,612,211 B1 | 12/2013 | Shires et al. | |
| 2005/0246165 A1 | 11/2005 | Pettinelli et al. | |
| 2007/0211141 A1* | 9/2007 | Christiansen | H04L 29/06027 348/14.08 |
| 2010/0060713 A1* | 3/2010 | Snyder | H04N 7/147 348/14.01 |
| 2010/0309284 A1 | 12/2010 | Samadani | |
| 2011/0270605 A1 | 11/2011 | Qin et al. | |
| 2011/0292162 A1 | 12/2011 | Byun et al. | |
| 2013/0124631 A1 | 5/2013 | Rosansky et al. | |
| 2013/0339875 A1* | 12/2013 | Sahai | H04L 12/1827 715/753 |

* cited by examiner

*Primary Examiner* — Yosef K Laekemariam (57) ABSTRACT

A teleconferencing system includes a dominance calculator (24), and a view engine (26). The dominance calculator (24) is configured to compute a dominance score for at least one channel of a plurality of channels of communication based on received video and/or audio from each communication channel. The view engine (26) is configured to send a display overlay including a visual indicator of the computed dominance score to the at least one channel.

18 Claims, 4 Drawing Sheets

SUPPORTING PATIENT-CENTEREDNESS IN TELEHEALTH COMMUNICATIONS

This application claims the benefit of U.S. Provisional Patent Application No. 62/010,120, filed on Jun. 10, 2014 which is hereby incorporated by reference herein.

The following relates generally to electronic conferencing. It finds particular application in conjunction with medical teleconferencing between healthcare practitioners and patients, and will be described with particular reference thereto. However, it will be understood that it also finds application in other usage scenarios and is not necessarily limited to the aforementioned application.

A traditional healthcare practitioner dominated communication model is typically one in which the practitioner listens to a patient's health complaints, provides a diagnosis, and issues instructions for the patient to follow. Patients are less likely to express all of their needs and/or complaints in a conversation in which the practitioner dominates the communication. The patient is less likely to follow the issued instructions, particularly instructions which conflict with practicalities in the life of the patient. In a patient centered model, the communication between the healthcare practitioner and the patient includes a balanced conversation. In the balance conversation, the relationship becomes a partnership in which the patient more freely expresses needs, concerns and doubts and participates in a selection among treatment options offered by the practitioner. By participating in the selection of a treatment the patient is more likely to follow the treatment steps.

Increasingly, with the cost reduction of voice and video communication, patients, often in a home or remote setting, are communicating with a healthcare by teleconferencing. The teleconferencing includes a video and audio communication channel in each direction. Each interface to a teleconferencing device typically includes a view of the video received from the other party, and a smaller view reflecting back the video being sent to the other party. For example, the healthcare practitioner has a view of the patient and a smaller reflected view of their own transmitted image. Similarly, the patient has a view of the healthcare practitioner and a smaller reflected view of their own transmitted image. The reflected view provides minimal feedback to the sending party in how they are being perceived by the other party. For example, a sending party will likely adjust their position to be seen or centered in the feedback screen, but typically receives no other feedback. Microphones collect the speech, which are directionally sent between the parties and provided to the receiving party by a speaker. However, research indicates that communication using technology tends to skew dominance further towards the practitioner.

A concern with processing confidential or privileged conversations, such as those between a doctor and a patient, is the recording or the storing of the conversation in whole or in part. For example, storing recordings of conversations raises concerns of security methods protecting the recordings, permitting access, storing and disposing of recordings, and the like. Additionally, recorded conversations can change what and how information is communicated by a party knowing they are being recorded.

The following discloses a new and improved mediated telehealth communication system which addresses the above referenced issues, and others.

In accordance with one aspect, a teleconferencing system includes a dominance calculator or means, and a view engine or means. The dominance calculator or means is configured to compute a dominance score for at least one channel of a plurality of channels of communication based on received video and/or audio from each communication channel. The view engine or means is configured to send a display overlay including a visual indicator of the computed dominance score to the at least one channel.

In accordance with another aspect, a method of teleconferencing includes receiving a plurality of channels of communication, each channel including streamed video and audio communications sent from a party. A dominance score for at least one channel of the plurality of channels of communication is computed based on the received video and/or audio from each communication channel. A display overlay including a visual indicator of the computed dominance score is sent to the at least one channel.

In accordance with another aspect, a computer includes a communications unit or means, a dominance calculator or means, and a view engine or means. The communications unit or means is configured to receive a plurality of communication channels and measure speech in the audio of each channel based on intensity and frequency thresholds. Each channel includes streamed audio and/or video from a party. The dominance calculator or means is configured to compute dominance scores relative to each of the communication channels based on the measured speech. The view engine or means is configured to send a display overlay on at least one channel, and the display overlay includes a visual indicator of the computed dominance score relative to the at least one channel.

One advantage is patient centeric communications.

Another advantage resides in feedback to participants in a teleconference concerning a balance of the communication.

Another advantage resides in suggestions to restore the balance in communication.

Another advantage resides in not recording or storing the conversation.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
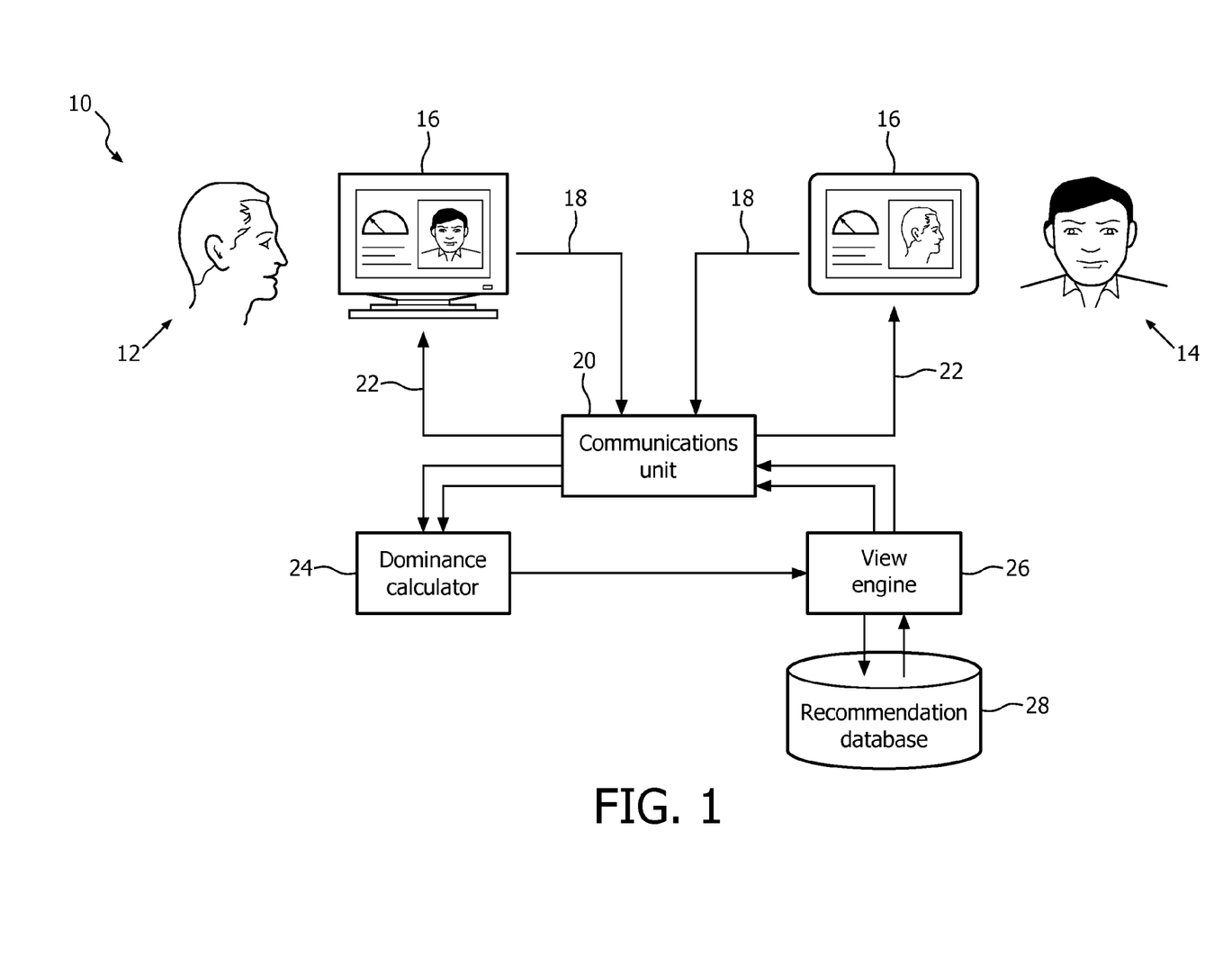
FIG. 1 diagrammatically illustrates an embodiment of a mediated telehealth communication system.

With reference to FIG. 1, an embodiment of a mediated telehealth communication system 10 is diagrammatically illustrated with communications between a healthcare practitioner 12 and a patient 14. Each party, such as the practitioner 12 and the patient 14, sends and receives audio and/or video communication through an audio/video (AV) device or means 16, such as a desktop computer, tablet computer, smart phone, television set and camera, a room augmented with audio/video capabilities, and the like. The AV devices 16 each transmit on a channel streamed audio and/or video of the respective party, e.g. video and audio of the patient conversing or video and audio of the practitioner conversing.

Each transmitted channel of audio and/or video is received by a communications unit or means 20, e.g. a channel from each party. The communication unit tracks each received channel and relays the audio and/or video to the corresponding AV device on a channel 22, e.g. the patient transmitted audio and/or video to the AV device of the practitioner. The communication unit can be part of each AV device, such as peer-to-peer communications or be part of a centralized communications device, such as a networked video over Internet Protocol (IP) server, or an appropriate configured room. For example, directional microphones with separate video cameras in a room with both parties, each distinguishing a different party are contemplated.

A dominance calculator or means 24 analyzes each channel and computes a relative dominance score by channel. For example, in a two party communication between a practitioner and a patient, a score is computed for the practitioner and a score is computed for the patient. The computed dominance score can include verbal and non-verbal measures or factors. For example, verbal measures can include length of time speaking, average length of speaking turn, number of interruptions, number of yields to an interruption, and the like. Length of time speaking, e.g. total time speaking indicates high dominance for greater time and low dominance with lesser time. Each channel is analyzed by intensity thresholds and frequency thresholds to classify time periods of the channel audio as speech or silence. The length of time speaking by a party is determined by a sum of the periods classified as speech. Average length of speaking turn is high when dominance is high and low when dominance is low. A speaking turn is a contiguous period of non-interrupted speech. For example, while party A speaks and party B is silent, time is accumulated for the speaking turn. The turn ends when party B speaks. The number of interruptions is larger for high dominance by a party and smaller for low dominance. Interruptions occur when the interrupting party speaks before the interrupted party stops speaking. Interrupts are measured with classified speech on channels which overlap. The interrupter and interrupted are determined based on an ordering of the speaking, e.g. party speaking turn before interruption. Yields, when a party stops speaking after the other party interrupts and allows the other party to continue speaking after interrupting, indicate high dominance for fewer yields and low dominance for more yields. Yields are measured by speech after an interruption and whether the party continues to speak, e.g. classified speech, or yields to the other party, e.g. classified silence.

In another example, non-verbal measures can include a number of times and/or duration of eye contact by a party, a measure of party posture, and the like. Sustained eye contact, e.g. for more than 3 seconds of a person looking into a face or video representation indicates high dominance, and aversive eye contact indicates low dominance. Eye contact can include the number of times of eye contact and/or the length of eye contact. Facial recognition and/or eye tracking are used to analyze frames of the streamed video to determine the amount and frequency of eye contact. Dominant posture is generally indicated by upright and forward posture which fills more of the visual field of a video display. As the conversation continues between parties, a less dominant posture can be indicated by sitting back further away from the camera, e.g. fills less of the visual display. Movement is another measure of posture which is calculated by taking a bitmap difference between successive video frames. Smiling is another measure of posture which is determined from facial recognition. Various postures can be classified as not attentive, lowly attentive, or very attentive which is used as a composite factor in the dominance score.

The dominance score is represented by $\Sigma \alpha_i x_i$ where $x_i$ is a measured verbal or non-verbal factor or a function of the verbal or non-verbal factor, and $\alpha_i$ is a weight or coefficient. The coefficients can be determined empirically from a sample of conversations subjectively scored by experts. The weight can include a cultural factor. For example, sustained eye contact is more strongly dominant in some cultures than others. The dominance score is continuously updated and can include a cumulative score and/or a moving window score, e.g. calculated based on the last n minutes of communication.

A view engine or means 26 constructs a display overlay of a visual indicator of the computed dominance score by channel. For example, a display overlay for the practitioner receives a first dominance score based on the relative dominance of the practitioner in the communication and a display overlay for the patient receives a second dominance score based on the relative dominance of the patient in the communication. The indicator can be a numerical representation, graph, or other visual means. The display is continuously or repeatedly updated and sent by the communications unit 20 to the corresponding AV device 16 along with the relay of the corresponding communication channel 22.

The view engine 26 based on each computed dominance score retrieves one or more written conversational suggestions from a database of suggestions 28. The database includes access by degree of dominance and/or role. For example, written suggestions for a practitioner to decrease their dominance can include "Ask an open ended question", "Reflect back what the patient is saying", or "Allow the patient to pause and think". To increase dominance, such as with a patient who is talking without listening, suggestions can include "Interrupt and ask for permission to make a suggestion to switch topics", or "Refer patient back to agenda items".

Example suggestions for a patient to increase dominance are "Ask a question (even a small one) to the doctor", "Describe your feelings in a little more detail", "The doctor is interested in what you are thinking now, Tell him what you are thinking", or "Tell the doctor how you really feel right now." Examples to decrease dominance of the patient include "Remember to answer the doctor's question", "Listen to what the doctor has to say and then tell him what you think", or "Try to focus on the points you agreed to discuss with your doctor".

The suggestions retrieved from the suggestion database 28 based on the computed dominance score are included in the display overlay by the view engine and sent to each channel 22. The AV device 16 receives the relayed audio/video channel 22 and displays the streamed video with the sent overlay of the visual indicator of the dominance score for the channel, and suggestions retrieved for that channel by the view engine 26.

Figure 2:
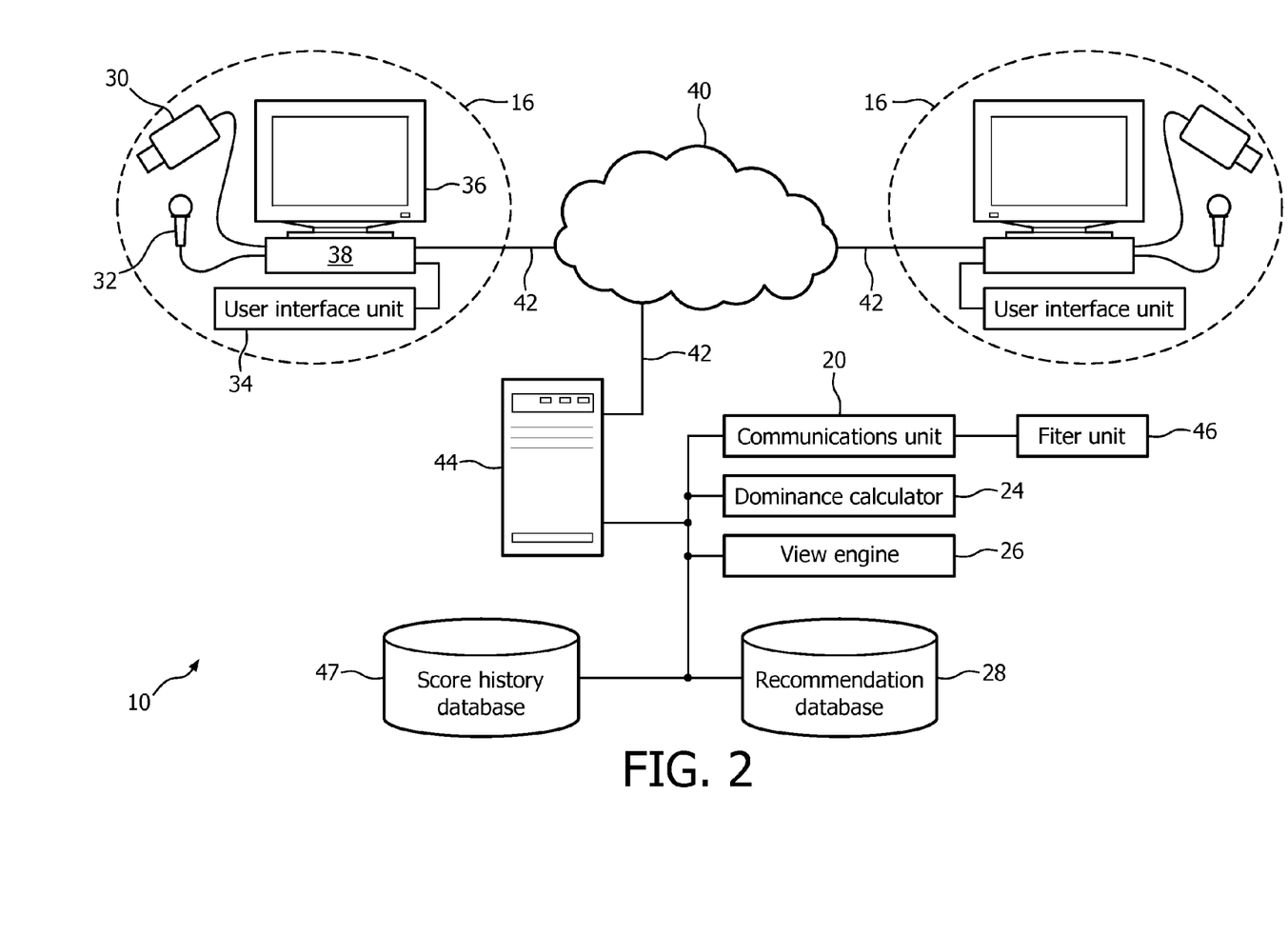
FIG. 2 schematically illustrates one embodiment of the mediated telehealth communication system.

With reference to FIG. 2, one embodiment of the mediated telehealth communication system 10 is schematically illustrated. Each AV device 16 includes a video camera or means 30 configured to generate video of a party and a microphone or means 32 to generate audio of a party. Each AV device 16 includes a user interface or means 34 configured to display on a display device 36 the video received on one channel, the generated video, and the display overlay of the indicator of the dominance score and retrieved suggestions. Each AV device includes a processor 38, such as an electronic or optical processor, field programmable gate array (FPGA), application specific integrated circuit (ASIC), and the like.

The AV devices 16 are communicatively connected by a network 40. The network can include wired or wireless communications, cellular or data communications, private or public networks, etc. The communication channels 42 connect to a server 44, such as a teleconferencing server. The channels of communication are received by the communications unit 20.

The communications unit 20 includes a filter unit or means 46 configured to blur the audio of incoming channels. The blurring facilitates classification of speech, e.g. easier average threshold identification, and to provide secure handling of the audio transmission. The relay of the streamed audio to the corresponding AV device is unaffected by the filter unit. For example, the inbound audio from the patient is filtered to blur the speech for analysis by the dominance calculator and the inbound audio is relayed to the practitioner as received inbound. Handling of the blurred speech by the server enhances privacy and reduces concerns over recordings.

A score history database 47 stores computed dominance scores. The computed dominance scores can be stored at selected intervals and/or termination of teleconference or communication. The view engine can summarize and/or analyze the dominance scores for a healthcare practitioner for individual teleconferences or communications or provide feedback across multiple teleconferences or communications. Changes in dominance scores over an individual conference, in different conferences across times of day, or days of week can provide indication of improvement, or indications of situations suggesting training. For example, the analysis can indicate a practitioner has problems with beginning teleconferencing sessions, ending teleconferences, teleconferencing at a particular time of day, etc. The view engine can provide summary information at the end of a teleconference which includes statistics and trends across multiple intervals in the individual session, e.g. every n minutes, or across multiple teleconferences for a given timeframe and/or number of sessions, e.g. the last week or last n sessions.

The various units, 20, 34, 46, dominance calculator 24, and view engine 26 are suitably embodied by a data processing device, such as the processor 38 of the AV devices 16, or by the network-based server computer 44 operatively connected with the AV devices 16 by the network 40, or so forth. Moreover, the disclosed communication streaming, display, display overlay, filtering, suggestion retrieval, and dominance calculation techniques are suitably implemented using a non-transitory storage medium storing instructions (e.g., software) readable by a data processing device and executable by the data processing device to perform the disclosed techniques.

Figure 3:
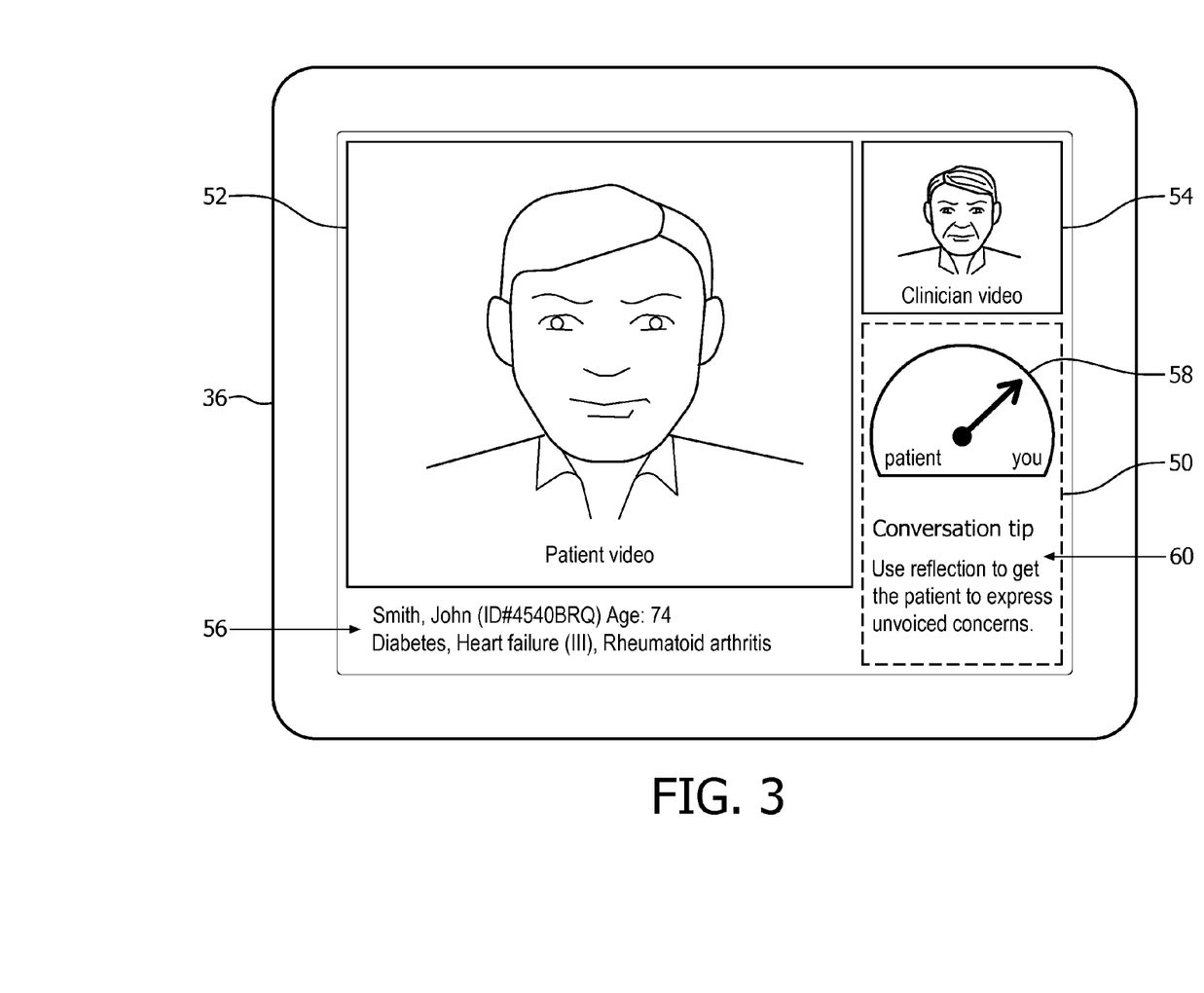
FIG. 3 illustrates an exemplary user interface and display overlay.

With reference to FIG. 3, an exemplary display device 36 with display overlay 50 is illustrated. The example illustrates the display as viewed by the practitioner. The received streamed video from the patient is displayed in a first window region or area 52. A second window region or area 54 displays the reflected video of the practitioner streamed to the patient. The display includes other party information 56, such as the patient name, patient ID, demographics, summary of complaints, diagnosis, etc.

The overlay 50 is displayed concurrently with the other display regions or areas. The overlay includes a visual indicator of the dominance score 58. The indicator includes a scale of the dominance score for ease of understanding, which indicates balance or dominance. The scale can further refine the dominance score, e.g. further delineations of dominance. In the example, an arrow points to a point on a scale indicative of the dominance score scaled between the patient and the practitioner. For example, if the arrow points vertically equally between the patient and practitioner, then the dominance score is balanced. In another example, the arrow pointing to the label "you" as the practitioner indicates that the practitioner is dominant. The degree of dominance is indicated by how closely the arrow is positioned to the "you" end of the scale and distance from the center or balanced dominance.

The overlay includes display written conversational suggestions 60 to increase or decrease dominance. In the example, the visual indicator of the dominance score points towards the practitioner indicating the practitioner is dominating the conversation, and a conversational suggestion "Use reflection to get the patient to express unvoiced concerns" is displayed in the overlay. The overlay can be formatted to fit within one or more regions of the display. For example, the visual indicator can be displayed in a separate region or area different from the conversational suggestions. The display can be arranged according to the characteristics of the AV device and/or user preferences.

The visual indicator is updated in the display as the conversation between the practitioner and patient progresses. The following table illustrates, with an example conversation, the change in dominance score and the display of suggestions. The example uses a function for the dominance score $ds=0.5a+0.3b+0.2c$ where a is a ratio of the speaking time of one party to the total time for all parties, b is a ratio of the number of turns of one party to the total of turns by all parties, and c is a ratio of the composite posture score to the total of composite scores by all parties.

| | Event | System Action | Cum. Dominance Score | Cumulative speaking time (seconds) | Cumulative # turns | Current Posture 1: not attentive 2: lowly attentive 3: very attentive |
|---|---|---|---|---|---|---|
| 1 | Conversation begins, clinician greets the patient and patient says "hello" | Begins to extract speech features for each speaker | Clinician: 70.5 Patient: 29.5 | Clinician: 20 Patient: 2 | Clinician: 1 Patient: 1 | Clinician: 3 Patient: 3 |
| 2 | Clinician starts the conversation and has been talking for the first 3 minutes, not letting the patient say much | Calculates ongoing dominance scores based on weighted features. | Clinician 79.5 Patient: 20.5 | Clinician: 200 Patient: 2 | Clinician: 2 Patient: 1 | Clinician: 3 Patient: 3 |
| 3 | Clinician pauses and patient asks a short question. | Calculates dominance score | Clinician: 72.2 Patient: 27.8 | Clinician: 200 Patient: 12 | Clinician: 2 Patient: 2 | Clinician: 3 Patient: 3 |
| 4 | Clinician responds to question and starts to give suggestions without trying to find out more about the patient's needs. Patient becomes slightly less attentive. | Calculates dominance score and then notices that doctor is trending to be too dominant (more than two turns with >70 dominance score), so system gives a suggestion to physician | Clinician: 78.1 Patient: 21.9 | Clinician: 300 Patient: 12 | Clinician: 3 Patient: 2 | Clinician: 3 Patient: 2 |

-continued

| Event | System Action | Cum. Dominance Score | Cumulative speaking time (seconds) | Cumulative # turns | Current Posture 1: not attentive 2: lowly attentive 3: very attentive |
|---|---|---|---|---|---|
| 5 | System looks up a recommendation from the database for the physician to lower his dominance. It selects a suggestion that lowers dominance by a large extent: reflection | | | | |
| 6 | Physician receives prompt on his screen: "Use reflection to check your understanding and have patient elaborate his needs." Physician reflects what the patient was saying. | Clinician: 78.1 Patient: 21.9 | Clinician: 305 Patient: 12 | Clinician: 3 Patient: 2 | Clinician: 3 Patient: 2 |
| 7 | Patient responds by talking more. | Clinician: 62.6 Patient: 37.4 | Clinician: 305 Patient: 100 | Clinician: 3 Patient: 3 | Clinician: 3 Patient: 3 |
| 8 | Physician hears a deeper concern that the patient has. He reflects the patient's thoughts again. | Clinician: 64.9 Patient: 35.1 | Clinician: 310 Patient: 100 | Clinician: 4 Patient: 3 | Clinician: 3 Patient: 3 |
| 9 | Patient agrees and elaborates. | Clinician: 52.9 Patient: 47.3 | Clinician: 310 Patient: 250 | Clinician: 4 Patient: 4 | Clinician: 3 Patient: 3 |
| # | Conversation continues. | System continues to measure ongoing dominance and intervenes when not balanced. | | | |

Figure 4:
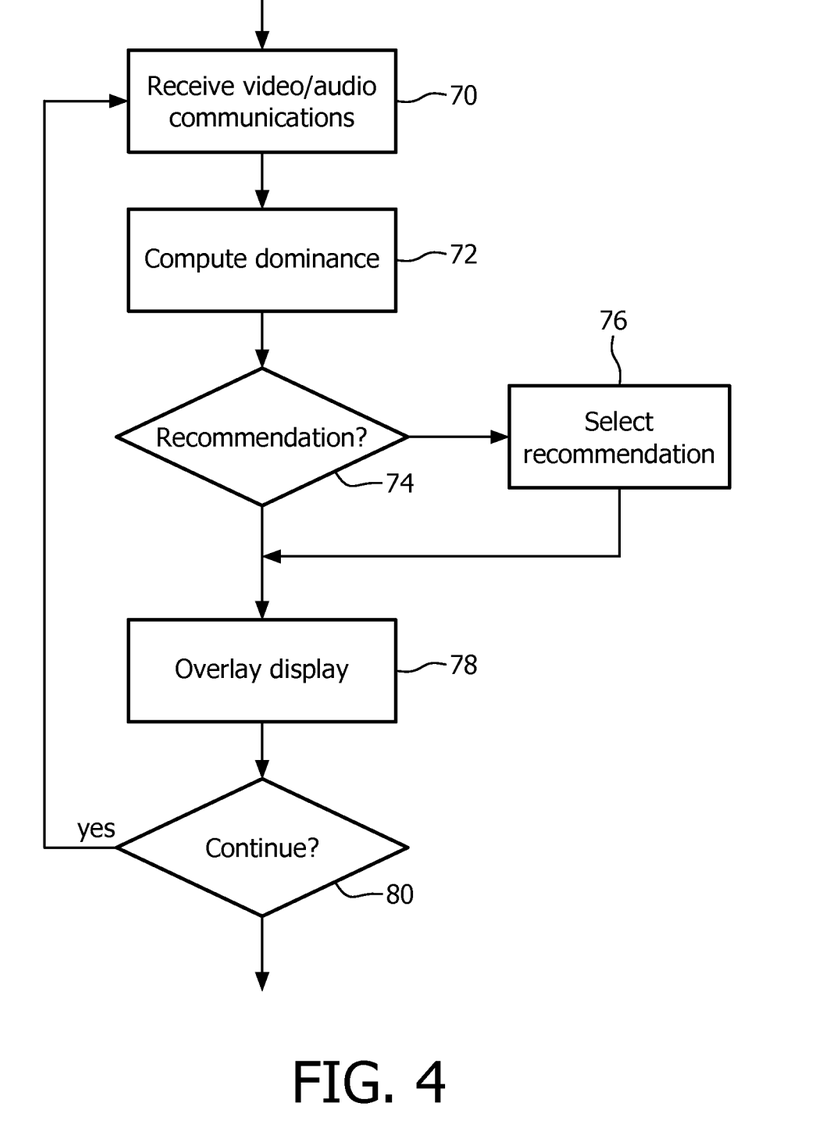
FIG. 4 flowcharts one method of mediated telehealth communications.

With reference to FIG. 4, one method of mediated telehealth communications is flowcharted. In a step or by a module 70, channels of communication are received. Each channel includes streamed video and/or audio sent by a party. Receiving a channel of communication can include blurring the speech and/or filtering the speech to classify the audio as silence or speech.

Dominance scores are computed for one or more of the channels of communication based on the received video and/or audio of each channel in a step or by a module 72. For example, the dominance score can be computed for the practitioner and not for the patient, but the computed score includes measures of both channels of communication. Computed dominance scores include verbal and/or non-verbal factors. For example, verbal factors include a length of time a party speaks, an average time of speaking turns by a party, a number of interruptions by a party, a number of yields to interruptions by a party, and the like. In another example, non-verbal factors include a number of times and/or duration of eye contact by a party, or a measure of posture, such as the amount of display area filled by a person, facial expressions, body posture, and the like. The factors include weights which can include a cultural factor or adjustment to the weighting.

In a decision step or by a module 74, the dominance scores are evaluated. Written conversational suggestions to increase or decrease dominance of a party are retrieved based on the evaluation of the computed dominance scores for each channel of the corresponding party in a step or by a module 76. The written suggestions are retrieved from a database of suggestions index for access by degree and direction of dominance and/or role. For example, access includes whether the retrieved suggestions increase or decrease dominance. The retrieved suggestions can be organized by role, e.g. patient, practitioner, and the like. The retrieval access can include a degree of dominance, such as strongly decrease dominance, decrease dominance, etc., or according to a predefined scale of dominance. For example, with the dominance scores scaled from 1 to 100 where 50 is a balanced score, and 100 is very dominant, the retrieval access can include a numerical range in the indexed access.

In a step or by a module 78, a display overlay is generated for one or more channels. The display overlay for the channel includes a visual indicator of the dominance score and the retrieved written conversational suggestions based on the dominance score for the corresponding channel. The display overlay is included in the corresponding relay of the channel of communication. The step can include storing the computed dominance score in the score history database 47.

In a decision step or by a module 80, the method steps repeat until the conversation ends or is otherwise terminated. The step can include recording of the final scores for training purposes. The steps can be performed by one or more processors or computing devices configured to perform the steps.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A teleconferencing system, comprising:
  a dominance calculator configured to compute a dominance score for at least one channel of a plurality of channels of communication, the dominance score indicating a degree of dominance of the at least one channel, the dominance score being calculated based on received video and/or audio from individual communication channels and based on non-verbal measures including duration of eye contact by a party, wherein sustained eye contact indicates high dominance; and
  a view engine configured to send a display overlay including a visual indicator of the computed dominance score to the at least one channel.

2. The system according to claim 1, further including:
  a database of written conversational suggestions indexed by dominance direction and degree; and
  wherein the view engine is further configured to retrieve at least one written conversational suggestion to the at least one channel to decrease or increase the computed dominance score from the database and include the at least one written conversational suggestion in the sent display overlay to the at least one channel.

3. The system according to claim 1, wherein the dominance calculator is further configured to compute the dominance score for the individual channels; and
  wherein the view engine is further configured to retrieve at least one written suggested action for the individual channels to balance the computed dominance score, and send the display overlay of individual visual indicators of the computed dominance score and the at least one written conversational suggestion to individual corresponding channels.

4. The system according to claim 1, further including:
  a communication unit configured to receive the plurality of channels of communication including an audio filter which blurs speech in the audio streamed communications.

5. A teleconferencing system, comprising:
  a dominance calculator configured to compute a dominance score for at least one channel of a plurality of channels of communication based on received video and/or audio from each individual communication channels and further based on a number of yields to interruptions by a party to another party; and
  a view engine or means configured to send a display overlay including a visual indicator of the computed dominance score to the at least one channel.

6. The system according to claim 5, wherein the interruptions of the party are measured with intensity and/or frequency thresholds.

7. The system according to claim 1, wherein the dominance score is further computed based on a cultural factor.

8. The system according to claim 1, wherein the dominance score is further computed based on at least one of:
  a most recent time period of a predetermined duration; or
  a cumulative time period.

9. The system according to claim 1, further including:
  a camera configured to generate the streamed video of one party;
  a microphone configured to generate the streamed audio of the one party;
  a display device configured to display the received video of another party and display the generated video of the one party; and
  a user interface unit configured for at least one channel to:
    receive and display the overlay of the indicator of the computed dominance score on the display device; or
    receive and display the overlay of the at least one written conversational suggestion on the display device.

10. A method of teleconferencing, comprising:
  receiving a plurality of channels of communication, individual channels including streamed video and audio communications sent from a party;
  computing a dominance score for at least one channel of the plurality of channels of communication, the dominance score indicating a degree of dominance of the at least one channel, the dominance score being computed based on the received video and/or audio from the individual communication channels and based on non-verbal measures including duration of eye contact by a party, wherein sustained eye contact indicates high dominance; and
  sending a display overlay including a visual indicator of the computed dominance score to the at least one channel.

11. The method according to claim 10, further including:
  retrieving at least one written conversational suggestion to the at least one channel to decrease or increase the computed dominance score from the database and including the at least one written conversational suggestion in the sent display overlay to the at least one channel.

12. The method according to claim 10, further including:
  computing the dominance score for the individual channels;
  retrieving at least one written suggested action for the individual channels to balance the computed dominance score; and
  sending the display overlay individual visual indicators of the computed dominance score and the at least one written conversational suggestion to the corresponding channels.

13. The method according to claim 10, wherein receiving includes blurring speech in the audio streamed communications.

14. A method of teleconferencing, comprising:
receiving a plurality of channels of communication, individual channels including streamed video and audio communications sent from a party;
computing a dominance score for at least one channel of the plurality of channels of communication based on the received video and/or audio from the individual communication channels and based on a number of yields to interruptions by a party to another party; and
sending a display overlay including a visual indicator of the computed dominance score to the at least one channel.

15. The system according to claim 1, wherein computing the
dominance score is based on at least one of:
a cultural factor;
a most recent time period of a predetermined duration; or
a cumulative time period.

16. A non-transitory computer-readable storage medium carrying software which controls one or more data processing devices to perform the method according to claim 10.

17. A data processing device configured to perform the method according to claim 10.

18. A computer, comprising:
a communications unit configured to receive a plurality of communication channels and measure speech in the audio of individual channels based on intensity and frequency thresholds, the individual channels including streamed audio and/or video from a party;
a dominance calculator configured to compute dominance scores relative to the individual communication channels, the dominance score indicating a degree of dominance of at least one channel the dominance score being calculated based on the measured speech and based on non-verbal measures including duration of eye contact by a party, wherein sustained eye contact indicates high dominance; and
a view engine configured to send a display overlay on the at least one channel, and the display overlay includes a visual indicator of the computed dominance score relative to the at least one channel.

* * * * *